United States Patent
Littmann et al.

[11] Patent Number: 5,957,842
[45] Date of Patent: *Sep. 28, 1999

[54] HIGH RESOLUTION INTRAVASCULAR SIGNAL DETECTION

[75] Inventors: Laszlo Littmann, Charlotte, N.C.; Liming Lau, Menlo Park; Omar Amirana, Palo Alto, both of Calif.

[73] Assignee: Cardima, Inc., Fremont, Calif.

[*] Notice: This patent is subject to a terminal disclaimer.

[21] Appl. No.: 08/488,132

[22] Filed: Jun. 7, 1995

Related U.S. Application Data

[60] Division of application No. 08/443,657, May 18, 1995, Pat. No. 5,699,796, which is a continuation-in-part of application No. 08/188,619, Jan. 27, 1994, Pat. No. 5,509,411.

[51] Int. Cl.$^6$ .......................................................... A61B 5/04
[52] U.S. Cl. ........................ 600/381; 600/585; 600/374; 607/122; 606/41
[58] Field of Search .................................. 128/642, 657, 128/692, 693, 772; 607/116, 119, 122–125; 606/41; 600/373–374, 377, 381, 585

[56] References Cited

U.S. PATENT DOCUMENTS

| | | |
|---|---|---|
| Re. 33,925 | 5/1992 | Bales et al. ................................ 606/48 |
| 452,220 | 5/1891 | Gunning . |
| 4,271,847 | 6/1981 | Stokes . |
| 4,332,259 | 6/1982 | McCorkle, Jr. . |
| 4,402,330 | 9/1983 | Lindemans . |
| 4,437,474 | 3/1984 | Peers-Trevarton . |
| 4,444,195 | 4/1984 | Gold ....................................... 128/642 |
| 4,449,528 | 5/1984 | Auth et al. . |
| 4,458,677 | 7/1984 | McCorkle, Jr. . |
| 4,481,953 | 11/1984 | Gold et al. ............................... 128/642 |

(List continued on next page.)

FOREIGN PATENT DOCUMENTS

| | | |
|---|---|---|
| 0 293 499 | 12/1988 | European Pat. Off. . |
| 0 369 044 | 5/1990 | European Pat. Off. . |
| 0366 127 | 5/1990 | European Pat. Off. . |
| 0387 453 | 9/1990 | European Pat. Off. . |
| 0 499 491 A2 | 8/1992 | European Pat. Off. . |
| 1813232 | 6/1969 | Germany . |
| 2 605 590 | 8/1977 | Germany . |
| 3718139C1 | 12/1988 | Germany . |
| WO 80/02801 | 12/1989 | WIPO . |
| WO 90/03151 | 4/1990 | WIPO . |

(List continued on next page.)

OTHER PUBLICATIONS

Lawrence T. Weston, M.D., et al., "A Prototype Coronary Electrode Catheter for Intracoronary Electrogram Recording," *The American Journal of Cardiology*, vol. 70, Dec. 1, 1992, pp. 1492 and 1493.

Repetto, et al., Transcoronary Epicardial Mapping of Accessory Pathways. Implications for Ablation Techniques. 10th Int'l. Cong., "The New Frontiers of Arrhythmias." Marilleva, Italy. Jan. 25–Feb. 1, 1992. pp. 475–480.

(List continued on next page.)

*Primary Examiner*—Jeffrey R. Jastrzab
*Attorney, Agent, or Firm*—Heller Ehrman White & McAuliffe

[57] ABSTRACT

A system for detecting electrical activity within a patient's heart comprising an elongated intravascular device, such as a catheter or guidewire, having a plurality of sensing electrodes on a distal section of the elongated device to detect electrical activity from within a blood vessel of the patient's heart. The intravascular device has a first compact array with a relatively small interelectrode spacing, such as less than 2 mm, and may have a second electrode array with an interelectrode spacing much greater than the interelectrode spacing in the first array. The second electrode array may be used to detect the general region of the arrhythmogenic tissue and the first electrode array is used to provide a high resolution of the electrical detection to more accurately pinpoint the location of the arrhythmogenic site. When the general region of the arrhythmogenic focus in known an intravascular device having a single array of electrodes with an interelectrode spacing of less than 2 mm may be used.

8 Claims, 4 Drawing Sheets

U.S. PATENT DOCUMENTS

| | | | |
|---|---|---|---|
| 4,559,951 | 12/1985 | Dahl et al. ............................ | 128/642 |
| 4,587,975 | 5/1986 | Salo et al. ............................ | 128/693 |
| 4,690,155 | 9/1987 | Hess . | |
| 4,777,955 | 10/1988 | Brayton et al. . | |
| 4,785,815 | 11/1988 | Cohen et al. ........................ | 128/642 |
| 4,840,186 | 6/1989 | Lekholm et al. . | |
| 4,867,173 | 9/1989 | Leoni ................................... | 128/772 |
| 4,869,248 | 9/1989 | Narula . | |
| 4,892,102 | 1/1990 | Astrinsky ............................ | 600/374 |
| 4,945,342 | 7/1990 | Steinemann .................... | 607/116 X |
| 4,945,912 | 8/1990 | Langberg ............................ | 128/642 |
| 4,955,382 | 9/1990 | Franz et al. ........................ | 128/642 |
| 4,957,110 | 9/1990 | Vogel et al. . | |
| 4,966,597 | 10/1990 | Cosman .............................. | 606/50 |
| 4,979,510 | 12/1990 | Franz et al. ........................ | 128/642 |
| 5,029,585 | 7/1991 | Lieber et al. ....................... | 128/642 |
| 5,044,375 | 9/1991 | Bach, Jr. et al. . | |
| 5,056,517 | 10/1991 | Fenici et al. . | |
| 5,069,215 | 12/1991 | Jadvar et al. ....................... | 128/642 |
| 5,083,565 | 1/1992 | Parins .................................. | 128/642 |
| 5,095,916 | 3/1992 | Smits . | |
| 5,095,917 | 3/1992 | Vancaillie ........................... | 128/831 |
| 5,099,917 | 3/1992 | Bardy . | |
| 5,104,393 | 4/1992 | Isner et al. .......................... | 606/15 |
| 5,122,136 | 6/1992 | Gugleilmi et al. ................. | 606/32 |
| 5,125,896 | 6/1992 | Hojeibane . | |
| 5,140,987 | 8/1992 | Schuger et al. . | |
| 5,159,937 | 11/1992 | Tremulis ............................. | 128/772 |
| 5,163,445 | 11/1992 | Chrisian et al. . | |
| 5,165,403 | 11/1992 | Mehra . | |
| 5,170,802 | 12/1992 | Mehra . | |
| 5,172,699 | 12/1992 | Svenson et al. .................... | 128/705 |
| 5,174,288 | 12/1992 | Bardy et al. . | |
| 5,184,621 | 2/1993 | Vogel et al. ........................ | 128/642 |
| 5,193,546 | 3/1993 | Shaknovich ................... | 128/662.06 |
| 5,193,550 | 3/1993 | Duffin ................................. | 128/697 |
| 5,199,433 | 4/1993 | Metzger et al. .................... | 128/642 |
| 5,215,103 | 6/1993 | Desai . | |
| 5,330,522 | 7/1994 | Kryenhagen ....................... | 607/122 |
| 5,341,807 | 8/1994 | Nardella ............................. | 128/642 |
| 5,364,352 | 11/1994 | Cimino et al. ..................... | 604/95 |
| 5,405,375 | 4/1995 | Ayers et al. ........................ | 607/122 |
| 5,445,148 | 8/1995 | Jaraczewski et al. ............. | 128/642 |
| 5,450,846 | 9/1995 | Goldreyer ........................... | 600/374 |
| 5,454,370 | 10/1995 | Avitall ................................. | 128/642 |
| 5,462,544 | 10/1995 | Saksena et al. .................... | 606/15 |
| 5,549,109 | 8/1996 | Samson et al. ..................... | 128/642 |
| 5,549,581 | 8/1996 | Lurie et al. ......................... | 604/282 |
| 5,673,695 | 10/1997 | McGee et al. ...................... | 128/642 |

FOREIGN PATENT DOCUMENTS

| | | |
|---|---|---|
| WO 92/21278 | 10/1992 | WIPO . |
| WO 93/08755 | 5/1993 | WIPO . |
| WO 93/08756 | 5/1993 | WIPO . |
| WO 93/08757 | 5/1993 | WIPO . |
| WO 93/08869 | 5/1993 | WIPO . |
| WO 93/20750 | 10/1993 | WIPO . |
| WO 94/06349 | 3/1994 | WIPO . |
| WO 94/16619 | 8/1994 | WIPO . |
| WO 95/09561 | 4/1995 | WIPO . |

OTHER PUBLICATIONS

Lesh, M.D., et al., Mapping in the Right Coronary Artery as an Aid to Radiofrequency Ablation of Right–Sided Accessory Pathways. NASPE Abstracts. *PACE*, vol. 14, Apr. 1991, Part II, p. 671, Abstract 213.

Hashimoto et al., "Significance of S–T Segment Elevations in Acute Myocardial Ischemia", *The American Journal of Cardiology*, vol. 37, pp. 493–500. (1976).

Swartz, M.D., et al., "Endocardial Atrial Catheter Ablation of Accessory Pathways After Intravascular Localization." NASPE Abstracts, *PACE*, vol. 13, Apr. 1990, p. 527, Abstract 126.

Fisher et al., "Nonsurgical Electrical Ablation of Tachycardias: Importance of Prior in Vitro Testing of Catheter Leads," *PACE* (1984) 7:74–81.

Inoue et al., "Intracoronary Ethyl Alcohol or Phenol Injection Ablates Aonitine–Induced Ventricular Tachycardia in Dogs", *J. Am. Coll. Cardiol.*, vol. 10, No. 6, Dec. 1987, pp. 1342–1349.

Szabo et al., "Localization of Accessory Pathways in the Wolff–Parkinson–White Syndrome", *PACE*, vol. 12, Oct. 1989, pp. 1691–1705.

DePaola et al., "Transcoronary Chemical Ablation of Ventricular Tachycardia in Chronic Chagasic Myocarditis", *J. Am. Coll. Cardiol.*, vol. 20, No. 2, Aug. 1992:480–482.

Michel Haissaguerre M.D., et al., "Closed–Chest Ablation of Retrograde Conduction in Patients with Atrioventricular Nodal Reentrant Tachycardia," *The New England Journal of Medicine*, Feb. 16, 1989, pp. 426–433.

Melvin M. Scheinman, M.D. et al., "Catheter Techniques for Ablation of Supraventricular Tachyardia," *The New England Journal of Medicine*, pp. 460–461. (1989).

Alden H. Harken, "Surgical Treatment of Cardiac Arrhythmias," *Scientific American*, Jul. 1993, pp. 68–74.

Walter, et al., Europ. Surg. Res. 3:130–138 (1971).

John J. Gallagher, et al., "Facilitation of Atrial Mapping by a New "Steerable" Catheter Electrode," Sanger Clinic and Carolinas Heart Institute, Charlotte, North Carolina, *Supplement II Circulation*, vol. 78, No. 4, Oct. 1988.

Warren M. Jackman, M.D., et al., "Direct Endocardial Recording from an Accessory Atrioventicular Pathway: Localization of the Site of Block, Effect of Antiarrhythmic Drugs, and Attempt at Nonsurgical Ablation," Pathophysiology and Natural History–Electrophysiology, *Circulation*, vol. 68, No. 5, Nov. 1983, pp. 906–916.

Brugada, et al., "Transcordary Chemical Ablation of Ventricular Tachycardia," *Circulation* (1989) 79:475–482.

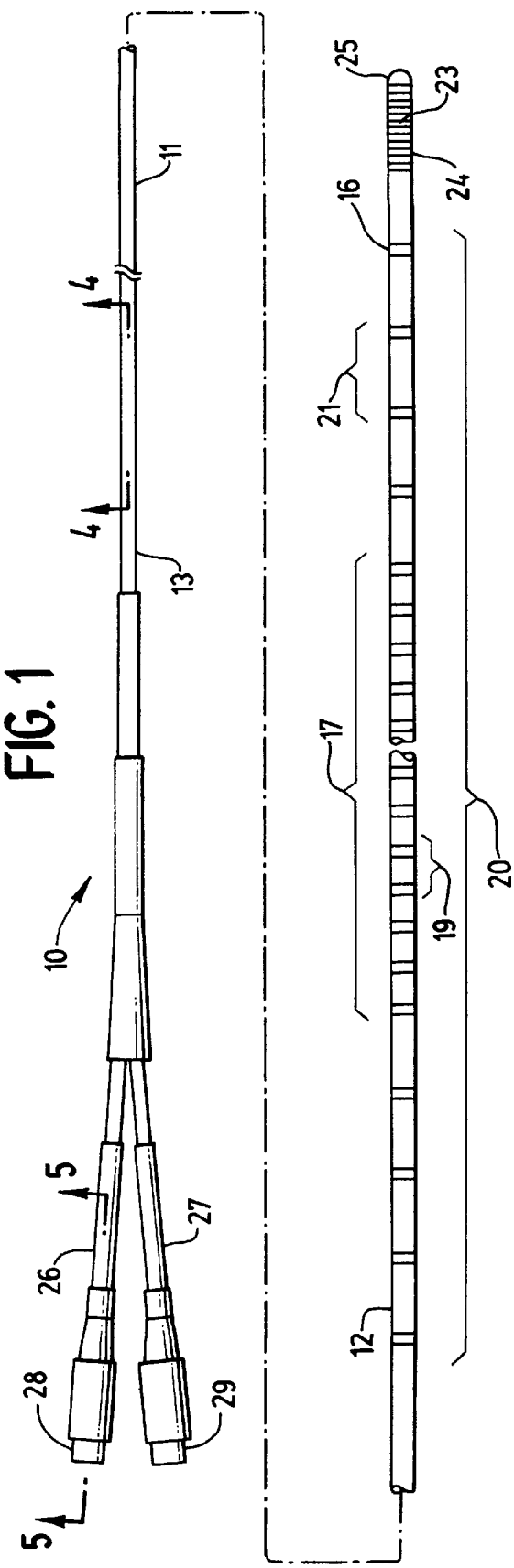
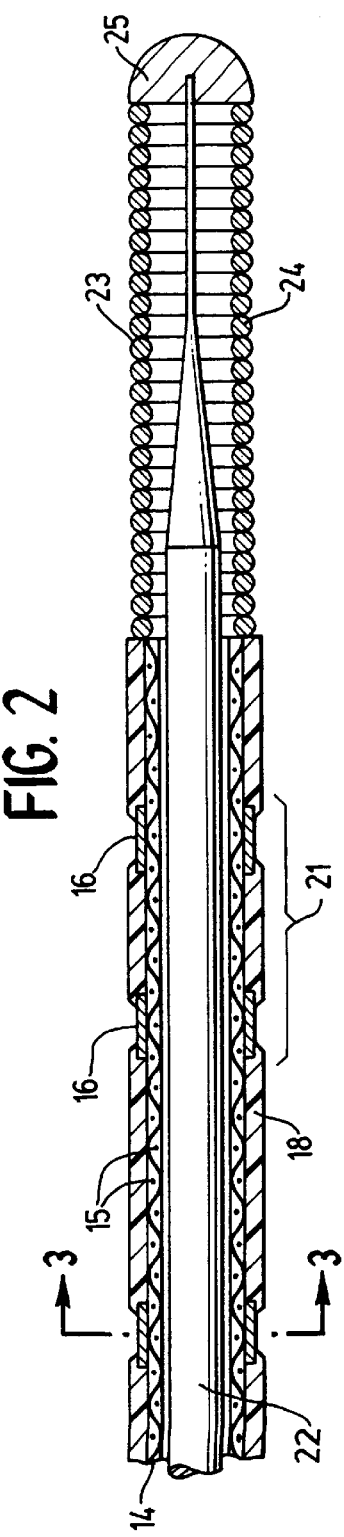

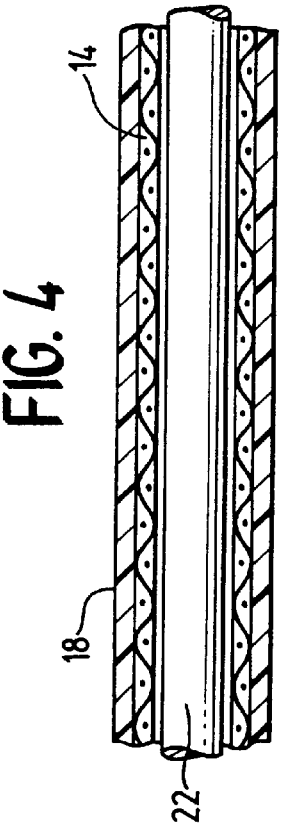
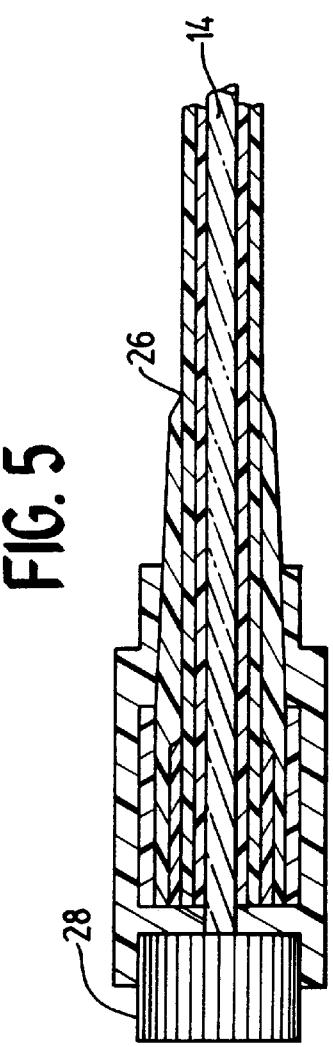
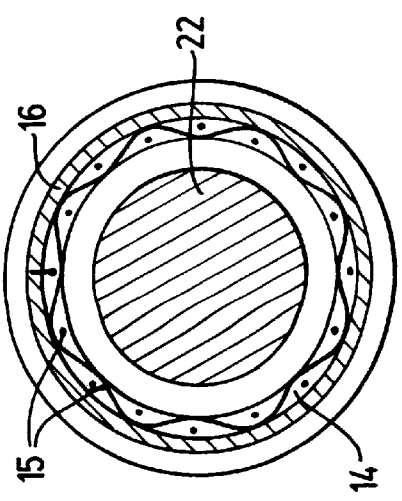

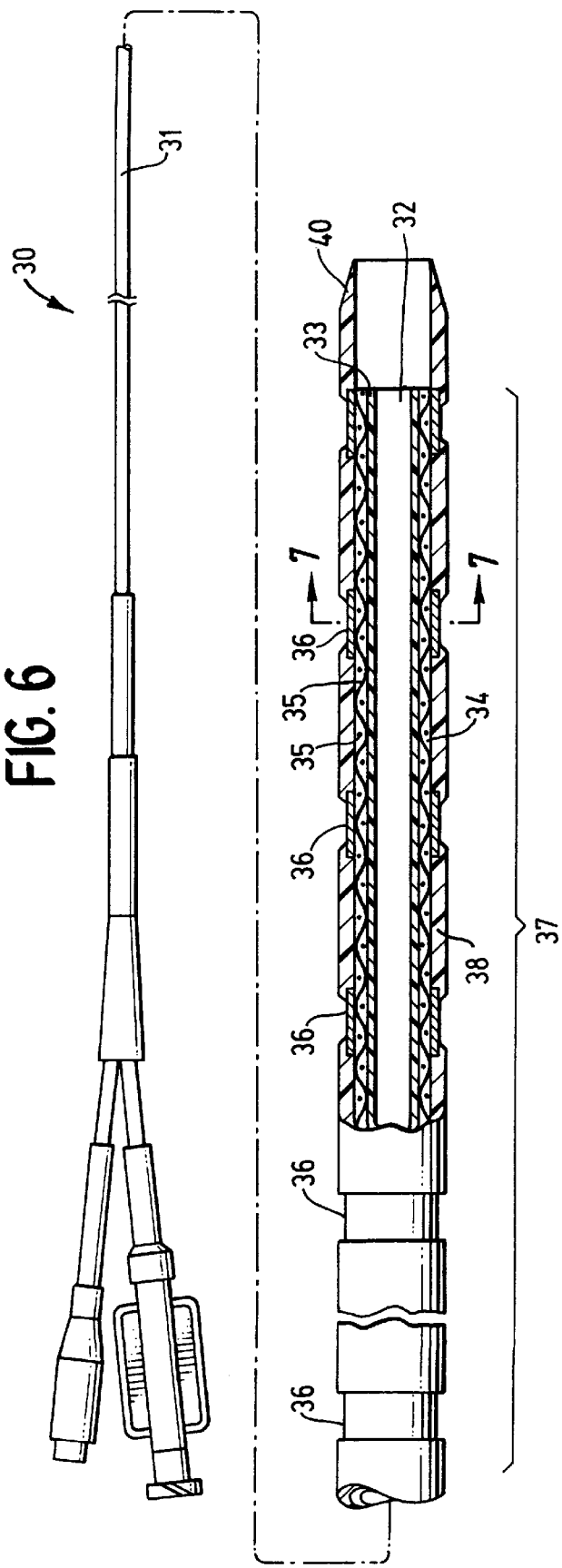

HIGH RESOLUTION INTRAVASCULAR SIGNAL DETECTION

RELATED APPLICATIONS

This application is a divisional application of application Ser. No. 08/443,657, filed May 18, 1995, now U.S. Pat No. 5,699,796, which is a continuation-in-part of application Ser. No. 08/188,619, filed Jan. 27, 1994, now U.S. Pat. No. 5,509,411 entitled INTRAVASCULAR SENSING DEVICE, which is incorporated herein by reference.

BACKGROUND OF THE INVENTION

This invention generally relates to a system for detecting electrical activity or signals of a patient's heart from within blood vessels thereof and particularly for determining the source of heart signals causing arrhythmia.

Prior methods for treating a patient's arrhythmia include the use of antiarrhythmic drugs such as sodium and calcium channel blockers or drugs which reduce the Beta-adrenergic activity. Other methods include the surgically sectioning the origin of the signals causing the arrhythmia or the conducting pathway for such signals. More frequently, however, the heart tissue which causes the arrhythmia is destroyed by heat, e.g. applying a laser beam or high frequency electrical energy, e.g RF or microwave, to a desired location on the patient's endocardium, in order to terminate the arrhythmia.

In the latter instance, the location of the tissue site causing or involved with the arrhythmia must be accurately known in order to be able to contact the desired location with a tissue destroying device. A major problem of ablating the site of the origin of the signals or a conductive pathway is to accurately determine the site so that an excessive amount of good tissue is not destroyed along with the arrhythmogenic site while ensuring that the arrhythmia does not return. For example, the average arrhythmogenic site consists of an area of about 1.4 $cm^2$ of endocardial tissue, whereas a re-entrant site might be much larger. RF ablation techniques produce lesions about 0.5 $cm^2$ in area, so several lesions may be necessary to completely ablate an area of interest. If the arrhythmogenic or re-entrant site is not accurately mapped, much good tissue surrounding the site will be unnecessarily destroyed.

A variety of methods have been used to detect electrical activity within a patient's heart to facilitate the mapping of electrical activity causing the arrhythmia. A number of U.S. Patents describe the use of elongated intravascular signal sensing devices which are advanced through the patient's vasculature until the distal portions of the sensing devices are disposed within one or more of the patient's heart chambers with one or more electrodes on the distal portion of the device in contact with the endocardial lining. While this procedure is widely used, it does not always allow the site of arrhythmogenic signals to be accurately determined.

The literature also mentions advancing an intravascular signal sensing device within a patient's coronary artery or coronary sinus or a cardiac vein. However, these methods appear to be experimental and have not been widely used clinically.

What has been needed is a method and system for accurately detecting the source of signals which cause the arrhythmia.

SUMMARY OF THE INVENTION

This invention is directed to an elongated intravascular sensing device for detecting electrical activity from within a lumen of a patients body. The device is suitable for detecting electrical activity from within a patient's vein or artery, such as electrical activity causing arrhythmia.

The intravascular sensing device of the invention comprises an elongated shaft with a proximal section and a distal section, with the distal section of the shaft being configured to be more flexible than the proximal section so as to be advanceable through tortuous anatomy, such as the patient', coronary arteries or cardiac veins. The device may also be used in other portions of the patient's body to locate electrical activity which may be involved with other conditions.

The flexible distal section of the sensing device is provided with a first array of sensing electrodes, e.g up to 16 or more electrodes, which may be bipolar electrodes for multipolar mode detection or independent electrodes for monopolar mode detection, which have a relatively small interelectrode spacing. In accordance with one aspect of the present invention, the electrodes in the first array have an interelectrode spacing which ranges from about 0.25 to about 2 mm, preferably about 0.5 to about 1.5 mm. The distal section may have a second array of sensing electrodes with an interelectrode spacing greater than the interelectrode spacing in the first array and generally about 2 to about 10 mm, preferably about 3 to about 8 mm. Alternate electrodes in the first array may be part of the second array of electrodes. The electrode spacing within an array of electrodes may vary, for example, the spacing at the extremities of the array may be larger than the spacing at the center of the array. However, for ease in analyzing the signals received from the sensing electrodes, it is preferred that the interelectrode spacing be uniform within an array. Both the spacing between electrode pairs and the spacing between the electrodes of the electrode pairs may be varied. The second array of sensing electrodes may be used to determine the general location of sensed electrical activity, such as an arrhythmogenic site, and the first array is then utilized to more accurately pinpoint the area of interest. When the general location of the electrical activity is already known, only the compact array of sensing electrodes needs to be used. When a bipolar or multipolar mode of sensing is to be used, the spacing between the electrodes of a pair of bipolar electrodes may be much less than the spacing between pairs of bipolar electrodes.

The shaft of the intravascular sensing device is preferably formed of a plurality of individually insulated electrical conductors braided or wound into an elongated tubular member with an inner lumen extending, therein. However, not all of the braided strands which make up the tubular member need be electrical conductors. Some may be high strength fibers such as nylon, Kevlar® and the like. The insulation on individual electrical conductors is exposed under each of the sensing electrodes to facilitate an electrical connection with the electrode. The electrical connection between the electrical conductor and the electrode may be secured by means of a suitable solder or brazing material, and the electrodes may be further secured to the underlying tubular member by a suitable adhesive to ensure maintenance of electrical contact with the exposed conductors.

The sensing electrodes may be circular bands about 0.25 to about 1 mm in width (the longitudinal dimension when on the device) and are preferably made from conducting material which is biocompatible with the body fluids such as gold.

A plastic jacket, preferably a lubricous polymer such as a thermoplastic fluoropolymer, is applied to the length of the braided tubular member with a slight overlap of the jacket over the edges of the individual electrodes to prevent exposure of a sharp metallic edge of the electrode which can cause damage to a blood vessel wall when the elongated device is advanced through a blood vessel. The entire circumference of an electrode need not be exposed. For example, the plastic jacket may be disposed about the distal shaft section on which the electrodes are mounted and holes may be made in the jacket to expose small portions of the underlying electrodes. The proximal ends of the electrical conductors are electrically connected to individual pins of a multi-pin connector on the proximal end of the shaft which is configured to be connected to a receiving member in electrical communication with a display unit which can display representations of the electrical activity sensed.

The elongated device of the invention may be in the form of a guidewire which has an elongated core member disposed within an inner lumen of the tubular member formed by the braided electrical conductors. The distal section of the guidewire may have a flexible guide tip which is distal to the length on which the sensing electrodes are mounted. The distal guide tip may have a helical coil which is disposed about the distal extremity of the core member or a separate shaping member, e.g. a ribbon, which extends from the distal extremity of the core member. The distal end of the core member or the separate shaping member may be manually shaped by the physician to facilitate steering the elongated sensing device within the patients vasculature by torquing the proximal end which extends out of the patient during the procedure. A smooth rounded tip or plug is provided at the distal end of the coil to avoid damage to a blood vessel when being advanced through the patient's vascular system. Conventional guidewire construction may be employed.

The elongated device of the invention may also be in the form of a catheter which has an elongated inner lumen extending from the proximal end to a discharge or guidewire port in the distal end of the device. The distal end of the catheter may be provided with a soft tip to minimize traumatic engagement with a blood vessel wall when being advanced therein. In one presently preferred embodiment, the inner lumen of the catheter form of the device is configured to allow the passage therethrough of a conventional guidewire or a guidewire version of the device of the invention which allows signal detection at different locations within the same blood vessel or branch thereof such as described in copending application Ser. No. 08/188,298, filed on Jan. 27, 1994, now U.S. Pat. No. 5,706,809 which is incorporated herein in its entirety.

When using the intravascular device of the invention, it is first introduced percutaneously by a conventional Seldinger technique or by means of a cut-down into a major peripheral artery or vein (e.g. the femoral vein or the femoral artery) and advanced through the vasculature to one or more desired locations within the veins or arteries of the patient's heart. The distal section of the elongated device of the invention is configured to be advanceable within blood vessels having a native inner diameter of less than about one millimeter and preferably less than 0.75 mm. A plurality of such elongated devices may be introduced into the patient's vascular system with an elongated device within one or more of the patient's cardiac veins and an elongated device within one or more of the patient's coronary arteries. The general location of the electrical activity may be first detected by means of the second electrode array having relatively large interelectrode spacing and the general location of the electrical activity is first determined. The electrical activity may then be detected by the electrodes of the first array which allows a much more accurate location of the site of the electrical activity.

With the device of the invention, electrical signals from the patient's heart are received by the plurality of sensing electrodes on the distal section and transmitted through electrical conductors attached to the individual electrodes to multipin connectors on the proximal ends of the shaft. The position of an elongated sensing device of the invention within an artery or vein of the patient's heart may be adjusted to optimize signal reception by the electrodes in the second array to roughly detect the location of the desired electrical activity and then the position may again be adjusted to provide a high definition signal reception by the more closely spaced electrodes in the first array. In this manner the location of the electrical activity may be pinpointed with much greater accuracy. The high resolution signal detection provided by the multiple array electrode system greatly facilitates the detection of electrical activity from arrhythmogenic sites or conducting pathways and the mapping thereof to detect the locations of such activity.

The elongated device of the invention provides substantially improved reception of electrical activity within the patient's heart without interference from electrical activity from other regions of the patient's heart. These and other advantages of the invention will become more apparent from the following detailed description of the invention and the accompanying exemplary drawings.

BRIEF DESCRIPTION OF THE DRAWINGS

FIG. 1 is an elevational view of an intravascular device having features of the invention.

FIG. 2 is an enlarged longitudinal cross-sectional view of a distal portion of the intravascular device shown in FIG. 1.

FIG. 3 is an enlarged transverse cross-sectional view of the distal portion of the intravascular device shown in FIG. 1 taken along the lines 3—3.

FIG. 4 is a longitudinal cross-sectional view of an intermediate portion of the intravascular device shown in FIG. 1 taken along the lines 4—4.

FIG. 5 is a longitudinal cross-sectional view of an extension of the proximal extremity of the intravascular device shown in FIG. 1 taken along the lines 6—6.

FIG. 6 is an elevational view, partially in section, of an alternative embodiment of the invention in the form of a catheter with a guidewire device disposed within the inner lumen of the catheter.

FIG. 7 is a transverse cross-sectional view of the catheter shown in FIG. 6 taken along the lines 7—7.

DETAILED DESCRIPTION OF THE INVENTION

Figure 8:
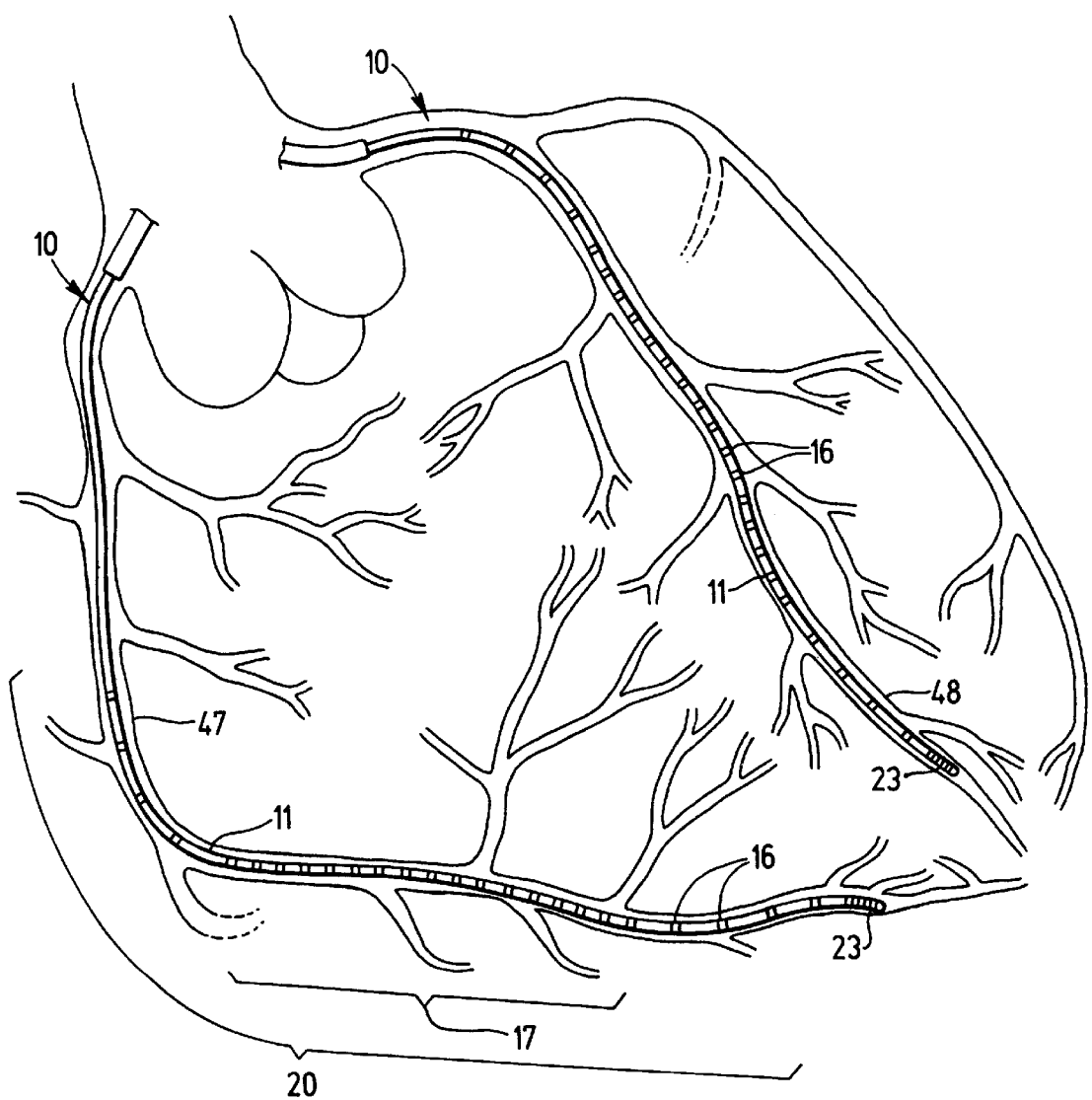
FIG. 8 is a schematic view of a patient's coronary arteries with one intravascular device as shown in FIG. 1 disposed within the right coronary artery and another disposed in the anterior interventricular branch of the left coronary artery.

Reference is made to FIGS. 1–5 which schematically illustrate an embodiment of the invention wherein the elongated intravascular device 10 includes shaft 11 with a distal section 12 and a proximal section 13. The shaft 11 has a braided tubular member 14 formed of a plurality of electrical conductors 15. The distal section 12 of the shaft 11 is provided with a plurality of sensing electrodes 16 which are arranged in a first array 17 of sensing electrodes with a relatively small interelectrode spacing 19 and a second array 20 of sensing electrodes with a second interelectrode spacing 21 which is much greater than the first interelectrode spacing. Every other sensing electrode 16 within the first array 17 may be common to the second array 20. A core member 22 is disposed within the inner lumen of the braided tubular member 14 and extends beyond the distal end thereof. A distal guide tip 23 includes a helical coil 24 disposed about and secured by suitable means, such as brazing, soldering or welding, to the distal extremity of the core member 22 and is provided with a smooth rounded distal end 25 formed by joining the distal tip of the coil 24 to the distal extremity of the core member 22. The distal extremity of the core member 22 is preferably flattened into a rectangular transverse cross section. An alternative "floppy" construction may be used where the distal extremity of the core member 22 terminates short of the distal end of the intravascular device and a shaping ribbon extends from the distal end of the core member 22 to the smooth rounded distal end 25.

FIG. 2 illustrates braided tubular member 14 with a single layer of braided strands. All of the strands in the layers need not be conductors 15, some may be formed of polymer materials such as nylon or Kevlar®. A plurality of braided layers may be employed, if needed, depending upon the number of sensing electrodes 16.

The proximal section 13 of the shaft 11 as shown in FIG. 1 has two extensions 26 and 27 which have multi-pin connectors 28 and 29 on the proximal ends thereof with each of the electrical conductors forming the braided tubular member 14 being electrically connected to a separate pin. Details of proximal extension 26 is depicted in FIG. 5 which includes pin connector 28.

FIGS. 6 and 7 schematically illustrate another presently preferred embodiment of the invention in the form of a catheter 30 with a catheter shaft 31 having an inner lumen 32 defined by an inner tubular element or lining 33, preferably formed of lubricous material such as Teflon® or other fluoropolymer. A braided tubular member 34 is disposed about tubular lining 33 and is formed of a plurality of individually insulated electrical conductors 35 which are electrically connected to individual sensing electrodes 36 as in the previously described embodiment. Some of the strands in the braided layers may be formed of other materials such as nylon. The sensing electrodes 36 are arranged in a compact array 37 with an interelectrode spacing of less than 2 mm, preferably less than about 1.5 mm. An outer polymer jacket 38 extends the length of the shaft 31 and the portion of the jacket extending beyond the distal end of the braided tubular member 34 is tapered to provide a nontraumatic flexible distal tip 38. As in the previously described example, the outer jacket 37 overlaps the leading and trailing edges of the electrodes 36 to avoid exposing a sharp metal edge when advancing or withdrawing the catheter through a patient's blood vessel.

The catheter 30 may be used to detect electrical activity from within the patient's coronary veins or arteries and then be used to direct fluids containing cardioplegic materials such as iced saline, solutions of KCl, lidocaine, procaineamide hydrochloride and the like to areas of the patient's heart which are suspected to be the origin of or to conduct aberrant signals causing arrhythmia. If the arrhythmia stops upon the delivery of a cardioplegic agent, then the operator is reasonably assured that the artery or vein through which the cardioplegic agent is delivered leads toward (in the case of an artery) or away from (in the case of a vein) the region of the patient's heart which is to be ablated in order to terminate the arrhythmia. The signal reception by the electrodes 36 are essentially the same as the signal reception for the first array in the previously described embodiment shown in FIGS. 1–5. Once the tissue causing the problem is located, high frequency electrical energy is emitted from the emitting electrode 17 to form a lesion in the tissue adjacent to the blood vessel and to thereby terminate the aberrant electrical activity.

The catheter 30 may be used in conjunction with a conventional guidewire or an intravascular device 10 as illustrated in FIGS. 1–5 where the guidewire or intravascular device is slidably disposed within the inner lumen 32 of the catheter. Adjustments in the relative locations of the intravascular device 10 and catheter 30 can be easily made by moving the intravascular device through the inner lumen 32 of the catheter 30 or moving the catheter over the guidewire or both.

When using a femoral artery or femoral vein approach to the patient's heart, it is frequently helpful to utilize a guiding catheter to guide the catheter or guidewire of the invention to the coronary artery ostium or the coronary sinus ostium as is done in other interventional coronary procedures, such as angioplasty. Typically, guiding catheters have specially shaped distal tips to facilitate the seating thereof within the desired ostium, thus eliminating the trouble of directing a catheter or guidewire of the invention into the desire ostium.

The sensing electrodes are typically gold bands with widths of about 0.25 to about 1 mm, typically about 0.5 mm, the longitudinal dimension when mounted on the intravascular device, which is just large enough to be fluoroscopically visible.

The overall length of the intravascular devices of the invention may range from about 80 to about 300 cm, typically about 120 to about 175 cm for delivery through the femoral artery or vein and about 90 to about 135 cm for delivery through the brachiocephalic artery or internal jugular vein. If the guidewire is to be advanced through the inner lumen of the catheter it should be longer than the catheter by about 20 to about 40 cm. The distal section of the catheter is about 3 to about 50 cm in length and is configured to be readily advanceable through a patient's coronary arteries or cardiac veins. The outer diameter of the catheter should be less than about 0.065 inch (1.7 mm) and preferably about 0.058 inch (4 Fr; 1.5 mm). The inner lumen 32 is about 0.012 to about 0.045 inch (0.3–1.1 mm) in diameter to facilitate the reception and advancement of a guidewire therethrough. The distal section of the guidewire is about 15 to about 40 cm in length and about 0.008 to about 0.022 inch (0.2–0.56 mm) in outer diameter to facilitate advancement through the coronary arteries and cardiac veins of a human being having natural diameters of less than 0.05 inch (1.27 mm), preferably less than 0.03 inch (0.76 mm). The distal guide tip on the guidewire is about 2 to about 10 cm in length and the coil is formed of wire about 0.0003 to about 0.006 inch (0.008–0.153 mm) in diameter. The core member of the guidewire may be tapered along its distal section as in conventional guidewire construction. The flattened distal extremity of the core member has a rectangular transverse cross section of about 0.002 by 0.006 inch (0.051–0.15 mm).

To the extent not previously described, the materials of construction of the various guidewire and catheter parts may be formed of conventional materials. The electrical conductors may be electrical grade copper wire about 0.005 inch (0.13 mm) in diameter which are provided with a thin insulated jacket or coating of polyimide or other suitable insulator. The outer jacket may be a thermoplastic fluoropolymer such as THV which is available from the 3M Corporation. The distal tip coil on the guidewire form of the invention is preferably formed of platinum to facilitate fluoroscopic observation thereof within the patient, but it may be formed in whole or in part with other material such as stainless steel, titanium, palladium, niobium, iridium and alloys thereof. The core wire of the guidewire may be formed of stainless steel or a superelastic NiTi type alloy, with the latter preferably having a stable austenite phase at body temperature and exhibiting a stress induced austenite-to-martensite phase transformation. Proximal and distal sections of the core member may be formed of different materials so as to provide a stronger proximal section for greater pushability and a more flexible distal section to facilitate passage through tortuous coronary anatomy.

One presently preferred method of using the elongated intravascular devices of the invention as shown in FIG. 8 wherein the distal portion 11 of the guidewires 10 such as shown in FIG. 1 are disposed within the right coronary artery and the anterior interventricular branch of the left coronary artery. As indicated, the electrodes 16 on the distal portion 11 extend along a major portion of the arteries in a first electrode array 17 where the interelectrode spacing is relatively small and a second electrode array 20 where the interelectrode spacing is greater than in the first array. As previously described alternate electrodes in the first array 17 may be; electrodes in the second array 20. The individual intravascular devices 10 may be moved within the arteries as needed to optimize the signals received by the electrodes 16. Signals from the electrodes 16 in the second array 20 are used to first detect the general region of the patient's heart from which the signals of interest originate. The intravascular device 10 may then repositioned to the extent necessary to place the first electrode array 17 as close as possible to the region of interest. The electrical activity from the desired region is then sensed by the electrodes 16 of the first array to more accurately locate the arrhythmogenic site. The detection of electrical activity by the intravascular devices 10 within both the right coronary artery and the anterior interventricular branch of the left coronary artery may be coordinated so that the region of interest can be located with the second electrode array of each device and then more accurately pinpointed by use of the first electrode array in both devices or the device closest to the region. While not shown in the drawings, the distal guide tip 23 may be shaped to facilitate entry into a side branch of the coronary artery.

It is within the ambit of this invention that the intravascular sensing device be introduced into a femoral artery or a femoral vein (or other convenient body access site) and be advanced through the patient's vasculature to the coronary veins or arteries. Once the intravascular device is situated in a proper location in the coronary vasculature, electrical activity may be received in any way that is appropriate for the specific situation. The catheter or guidewire may be moved to another location and another set of signals received. It should be apparent that since each electrode mounted on the distal section of the sensing device is individually brought out via the woven wires or filaments to the electrical connection at the proximal end, that each electrode may be used in conjunction with any other electrode in a bipolar mode or they may be used in a monopolar mode. The sensing devices may be used in multiples, e.g., a sensing device in each of the major coronary veins and arteries, as shown in FIG. 8, to provide an overall and complete electrical map of the heart. In this way, arrhythmic foci may be readily located and therapeutic action taken.

Although individual features of one embodiment of the invention may be described herein and shown in one or more of the drawings and not in others, those skilled in the art will recognize that individual features of one embodiment of the invention can be combined with any or all the features of another embodiment of the invention. Additionally, various modifications and improvements may be made to the invention without departing from the scope thereof.

What is claimed is:

1. An elongated intravascular catheter for detecting electrical activity of a patient's heart from within a blood vessel of the patient's heart, comprising:

a) an elongated shaft having a distal end, proximal and distal sections, an inner lumen extending therein and the distal section having a maximum outer diameter of less than about 0.56 mm to be advanceable through a vein or artery of a patient's heart;

b) a longitudinally arranged array of at least four sensing electrodes spaced a distance from the distal end of the shaft, having axial lengths of about 0.25 to about 1 mm mounted on a length of the distal section having a substantially uniform interelectrode spacing of about 0.25 to about 0.75 mm;

c) a core member within the shaft lumen;

d) electrical conductors which transmit electrical activity sensed by the individual electrodes in the array of sensing electrodes; and e) an electrical connector on a proximal extremity of the shaft electrically connected to the electrical conductors.

2. The intravascular catheter of claim 1 wherein the elongated shaft is a tubular member formed by strands which include individually insulated electrical conductors.

3. The intravascular catheter of claim 2 where the strands of the tubular member are braided.

4. The intravascular catheter of claim 2 wherein the tubular member has a tubular lining which defines the inner lumen extending therein.

5. The intravascular catheter of claim 4 wherein the tubular lining is formed of a lubricous material.

6. The intravascular catheter of claim 5 wherein the lubricous material is a fluoropolymer.

7. The intravascular catheter of claim 1 wherein the electrodes in the array have an interelectrode spacing of about 0.5 to about 0.75 mm.

8. The intravascular catheter of claim 1 wherein a flexible member is disposed about a distal extremity of the core member distal to the electrodes.

* * * * *